(12) United States Patent
Assmann et al.

(10) Patent No.: US 6,552,056 B2
(45) Date of Patent: Apr. 22, 2003

(54) ISOTHIAZOLECARBOXAMIDES AND THEIR USE AS MICROBICIDES

(75) Inventors: Lutz Assmann, Langenfeld (DE); Yoshinori Kitagawa, Tochigi (JP); Koichi Ishikawa, Tochigi (JP); Daiei Yamazaki, Tochigi (JP); Haruko Sawada, Ibaraki (JP); Yasuo Araki, Tochigi (JP); Haruhiko Sakuma, Tochigi (JP); Taro Kinbara, Tochigi (JP); Kinya Imanishi, Saitama (JP)

(73) Assignee: Nihon Bayer Agrochem K.K., Tokyo (JP)

( * ) Notice: Subject to any disclaimer, the term of this patent is extended or adjusted under 35 U.S.C. 154(b) by 0 days.

(21) Appl. No.: 09/979,856

(22) PCT Filed: Nov. 26, 2001

(86) PCT No.: PCT/EP00/04423

§ 371 (c)(1),
(2), (4) Date: Nov. 26, 2001

(87) PCT Pub. No.: WO00/73290

PCT Pub. Date: Dec. 7, 2000

(65) Prior Publication Data

US 2003/0013750 A1 Jan. 16, 2003

(30) Foreign Application Priority Data

May 28, 1999 (JP) .................................. 11-150185

(51) Int. Cl.[7] .................. A01N 43/80; C07D 275/03
(52) U.S. Cl. .............................. 514/372; 548/214
(58) Field of Search ........................ 548/214; 514/372

(56) References Cited

U.S. PATENT DOCUMENTS

| 4,980,363 A | 12/1990 | Shimotori et al. ........... 514/365 |
|---|---|---|
| 5,039,694 A | 8/1991 | Suzuki et al. ............... 514/406 |
| 5,104,886 A | 4/1992 | Shimotori et al. ........... 514/365 |
| 5,240,951 A | 8/1993 | Shimotori et al. ........... 514/372 |
| 6,277,791 B1 | 8/2001 | Assmann et al. ............ 504/269 |
| 6,372,692 B1 * | 4/2002 | Assman ...................... 548/214 |

FOREIGN PATENT DOCUMENTS

| DE | 99/24413 | 5/1999 |
|---|---|---|
| EP | 73 973 | 3/1983 |
| EP | 313 091 | 4/1989 |
| JP | 60-139672 | 7/1985 |
| JP | 1-121263 | 5/1989 |
| JP | 1-199963 | 8/1989 |

* cited by examiner

*Primary Examiner*—Robert Gerstl
(74) *Attorney, Agent, or Firm*—Richard E. L. Henderson; Raymond J. Harmuth

(57) ABSTRACT

Isothiazolecarboxamides of the formula:

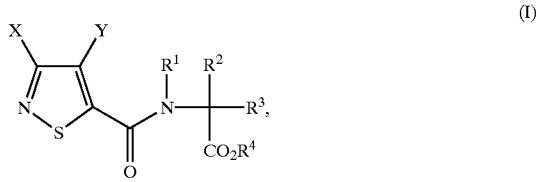

(I)

wherein X, Y, $R^1$, $R^2$, $R^3$ and $R^4$ have the meanings given in the specification, may be used as microbicides.

13 Claims, No Drawings

ISOTHIAZOLECARBOXAMIDES AND THEIR USE AS MICROBICIDES

FIELD OF THE INVENTION

The present invention relates to novel isothiazolecarboxamides, to processes for their preparation and to their use as microbicides.

BACKGROUND OF THE INVENTION

It has been already known that certain isothiazolecarboxamides can be employed for the control of plant pests (see JP-A 119 463/1988, JP-A 121 263/1989, JP-A 199 963/1989, JP-A 149 572/1990, JP-A 59 024/1993 and DE-A 31 33 418). Further, a process for the preparation of certain isothiazolecarboxamides and the use of such compounds as aarochemicals or as intermediates have also been disclosed already (see JP-A 139 672/1985). The fungicidal activity of such known compounds, however, is not always satisfactory.

DETAILED DESCRIPTION

There have now been found novel isothiazolecarboxamides of the formula

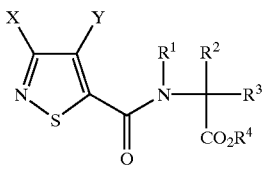

(I)

wherein

X represents halogen, $C_{1-4}$ alkyl or $C_{1-4}$ haloalkyl,

Y represents a hydrogen atom, halogen, cyano or $C_{2-5}$ alkoxycarbonyl, $R^1$, $R^2$ and $R^4$ independently of one another represent a hydrogen atom or $C_{1-4}$ alkyl, and $R^3$ represents a hydrogen atom, $C_{1-12}$ alkyl, $C_{3-8}$ cycloalkyl, optionally substituted $C_{2-6}$ alkenyl, $C_{5-8}$ cycloalkenyl, $C_{7-8}$ bicycloalkenyl, $C_{1-4}$ haloalkyl, substituted $C_{1-4}$ alkyl, optionally substituted phenyl, optionally substituted naphthyl or optionally substituted 5- or 6-membered heterocyclyl having 1 to 3 heteroatoms selected from the group consisting of nitrogen, oxygen and sulphur, which heterocyclyl group may also be benzo-condensed, or $R^2$ and $R^3$, together with the carbon atom to which they are bonded, form an optionally substituted 5- or 6-membered hydrocarbon ring or an optionally substituted 5- or 6-membered heterocyclic ring comprising at least one nitrogen atom, or $R^2$ and $R^3$, together with the carbon atom to which they are bonded, form a group of the formula C=CH—$R^5$, in which $R^5$ represents hydrogen or $C_{1-2}$ alkyl, or $R^3$ and $R^4$, together with the carbon atom and the carboxyl group to which they are bonded, form a 5- or 6-membered heterocyclic ring having at least one ring-constituting oxygen atom and being substituted with at least one oxo group, with the proviso, however, that $R^3$ does not represent isopropyl, if X and Y represent chloro, $R^1$ and $R^2$ represent a hydrogen atom and $R^4$ represents $C_{1-4}$ alkyl Further, it has been found that the isothiazolecarboxamides of the formula (I) can be prepared by a) reacting isothiazolecarboxylic acid chlorides of the formula

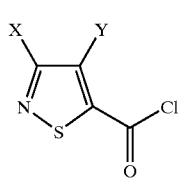

(II)

in which

X and Y have the above-mentioned meanings, with amines of the formula

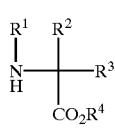

(III)

in which $R^1$, $R^2$, $R^3$ and $R^4$ have the above-mentioned meanings, in the presence of an inert diluent and, if appropriate, in the presence of an acid binding agent and, if appropriate, in the presence of a phase-transfer catalysts, or b) reacting isothiazolecarboxylic acid derivatives of the formula

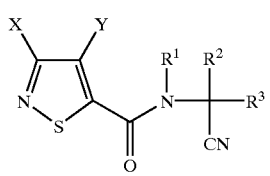

(IV)

in which

X, Y, $R^1$, $R^2$ and $R^3$ have the above-mentioned meanings, with compounds of the formula

HO—$R^4$ (V)

in which $R^4$ has the above-mentioned meanings, in the presence of an inert diluent and, if appropriate, in the presence of an acid catalyst, or c) reacting isothiazecarboxamides of the formula

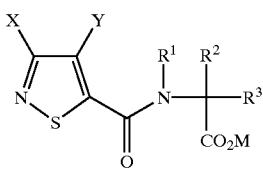

(Ia)

in which
X, Y, R$^1$, R$^2$ and R$^3$ have the above-mentioned meanings and
M represents C$_{1-4}$ alkyl,
with water, if appropriate, in the presence of an inert diluent and, if appropriate, in the presence of an acid binding agent or in the presence of an acid catalyst and, if appropriate, in the presence of a phase-transfer catalyst.

Finally, it has been found that the isothiazolecarboxamides of the formula (I) are outstandingly active as microbicides in agriculture and horticulture, particularly as fungicides for the direct control of plant diseases or for causing resistance in plants against plant pathogens.

Surprisingly, the isothiazolecarboxamides according to the invention have a much better microbicidal activity than the already known compounds, which are structurally most similar and have the same type of action.

In the present context "halogen" represents fluoro, chloro, bromo or iodo.

"Alkyl" represents straight-chain or branched groups, such as methyl, ethyl, n- or iso-propyl, n-, iso, sec- or tert-butyl, n-pentyl, iso-pentyl, tert-amyl, pentan-3-yl, neopentyl, n-hexyl, n-heptyl, n-octyl, n-nonyl, n-decyl, n-undecyl and n-dodecyl.

"Alkoxy" represents straight-chain or branched groups, such as methoxy, ethoxy, n-or iso-propoxy, n-, iso-, sec- or tert-butoxy etc.

"Alkylthio" represents straight-chain or branched groups, such as methylthio, ethylthio, n- or iso-propylthio, n-, iso-, sec- or tert-butylthio etc.

"Alkylsulfinyl" represents straight chain or branched groups, such as methylsulfinyl, ethylsulfinyl, n- or iso-propylsulfinyl, n-, iso-, sec- or tert-butylsulfinyl etc.

"Alkylsulfonyl" represents straight-chain or branched groups, such as methyl-sulfonyl, ethylsulfonyl, n- or iso-propylsulfonyl, n-, iso-, sec- or tert- butylsulfonyl etc.

"Alkoxycarbonyl" represents straight-chain or branched groups, such as methoxy-carbonyl, ethoxycarbonyl, n- or iso-propoxycarbonyl, n-butoxycarbonyl etc.

"Alkylenedioxy" represents groups, in which the alkylene part is straight-chain or branched, and includes methylenedioxy, ethylenedioxy, methylmethylenedioxy, dimethylmethylenedioxy, propylenedioxy, tetramethylethylenedioxy etc.

"Alkenylidene" represents a bivalent group, in which the carbon atom in position 1 is double bonded with the carbon atom in position 2. As examples there may be mentioned vinylidene, 1-propenylidene, 1-butenylidene etc.

"Cycloalkyl" represents a cyclic alkyl group and includes, for example, cyclopropyl, cyclobutyl, cyclopentyl, cyclohexyl, cycloheptyl, cyclooctyl etc.

"Alkenyl" represents straight-chain or branched groups and includes, for example, vinyl, allyl, 1-propenyl, 1-methylvinyl, 2-methyl-1-propenyl, 1-butenyl, 1-pentenyl, 1-hexenyl etc.

"Cycloalkenyl" represents a cyclic alkenyl group and includes, for example, cyclo-butenyl, cyclopentenyl, cyclohexenyl, cycloheptenyl, cyclooctenyl etc.

"Bicycloalkenyl" represents a bicyclic alkenyl group and includes, for example, bicyclo[2.2.1]-2-heptenyl, bicyclo[2.2.1]hepta-2,5-dienyl, bicyclo[2.2.2]octadienyl etc.

"Haloalkyl" represents straight-chain or branched alkyl groups, which are substituted with one or more halogen atoms, preferably fluoro, chloro and/or bromo. As examples there may be mentioned trifluoromethyl, 2-fluoroethyl, 2-chloroethyl, 2-bromoethyl, 2,2,2-trifluoroethyl, 2,2,2-trichloroethyl, 3-chloropropyl, 3-bromopropyl, 1-chloropropan-2-yl, 1-bromopropan-2-yl, 1,3-difluoropropan-2-yl, 2,3-dibromopropyl, 2,2-dichloro-3,3,3-trifluoropropyl etc.

As substituents of "alkyl" and "allenyl" there may be mentioned hydroxy; alkoxy such as methoxy, ethoxy, n- or iso-propoxy, n-butoxy etc.; mercapto; alkylthio such as methylthio, ethylthio, n- or iso-propylthio, n-butylthio etc.; alkylsulfinyl such as methylsulfinyl, ethylsulfinyl, n- or iso-propylsulfinyl, n-butylsulfinyl etc.; alkyl-sulfonyl such as methylsulfonyl, ethylsulfonyl, n- or iso-propylsulfonyl, n-butylsulfonyl etc.; phenyl; a 5-membered heterocyclic group which has 1–3 nitrogen atoms and may be benzo-condensed such as a univalent group derived from pyrrolidine, imidazolidine, pyrrole, imidazole, pyrazole, indole, benzimidazole etc.

"Phenyl" and "naphthyl" may be substituted with one or more substituents and if substituted with a plurality of substituents, these substituents may be identical or different. As examples of the substituents there may be mentioned halogen such as fluoro, chloro, bromo and iodo; alkyl such as methyl, ethyl, n- or iso-propyl, n-, tert-, sec-, or iso-butyl etc.; alkoxy such as methoxy, ethoxy, n- or iso-propoxy, n-, tert-, sec- or iso-butoxy etc.; alkylthio such as methylthio, ethylthio, n- or iso-propylthio, n-, tert-, sec- or iso-butylthio etc.; alkylenedioxy such as methylenedioxy, ethylene-dioxy, methylmethylenedioxy, dimethylmethylenedioxy, propylenedioxy, tetra-methylethylenedioxy etc.; di-C$_{1-4}$ alkylamino such as dimethylamino, N-methyl-N-ethylamino, diethylamino, N-ethyl-N-propylamino, diisopropylamino, dibutylamino etc.; haloalkyl such as trifluoromethyl, 2,2,2-trifluoroethyl, 2,2,2-trichloroethyl etc.; benzyloxy, phenoxy, nitro, cyano and phenyl.

A "5- or 6-membered hydrocarbon ring" may be a saturated or an unsaturated group and includes, for example, cycloalkane such as cyclopentane, cyclohexane etc.; cycloalkene such as cyclohexene etc. These hydrocarbon rings may be substituted with alkyl such as, for example, methyl, ethyl, n- or iso-propyl etc.

A "5- or 6-membered heterocyclic group" includes a "5- or 6-membered saturated heterocyclic group" and a "5- or 6-membered aromatic heterocyclic group" having 1–3 heteroatoms selected from the group consisting of nitrogen, oxygen and sulfur.

As "5- or 6-membered saturated heterocyclic group" there may be mentioned univalent groups derived from, for example, pyrrolidine, tetrahydrofuran, imidazolidine, pyrazolidine, piperidine, tetrahydropyran, piperazine, morpholine, 1,3-dioxolane etc. These heterocyclic groups may be substituted with, for example, hydroxy, halogen (for example, fluoro, chloro, bromo etc.), oxo, thioxo, alkyl (for example, methyl, ethyl, n- or iso-propyl, n-, sec-, iso-, or tert-butyl etc.), alkoxy (methoxy, ethoxy, n- or iso-propoxy etc.), alkylthio (for example, methylthio, ethylthio, n- or iso-propylthio etc.), alkoxyalkyl (for example, methoxymethyl, ethoxymethyl etc.), alkylthioalkyl (for example, methylthiomethyl, ethylthiomethyl etc.), and in case a plurality of substituents is present, they may be identical or different.

As "5- or 6-membered aromatic heterocyclic group" there may be mentioned univalent groups derived from, for example, furan, pyrrole, thiophene, imidazole, pyrazole, oxazole, isoxazole, thiazole, isothiazole, 1,2,4-triazole, 1,3,4-thiadiazole, pyridine, pyridazine, pyrimidine, pyrazine etc. These heterocyclic groups may be substituted with, for example, cyano, nitro, halogen (for example, fluoro, chloro, bromo etc.), allcyl (for example, methyl, ethyl, n- or iso-propyl, n-, sec-, iso-, or tert-butyl etc.), alkoxy (for example, methoxy, ethoxy, n- or iso-propoxy etc.), alkylthio (for example, methylthio, ethylthio, n- or iso-propylthio etc.), haloalkyl (for example, trifluoromethyl etc.), baloalkoxy (for example, trifluoromethoxy etc.), cyanoalkyl (for example, cyanomethyl, 1-cyanoethyl, 1-cyanopropyl etc.), alkoxycarbonyl (for example, methoxycarbonyl, ethoxycarbonyl etc.), alkoxyalkyl (for example, methoxymethyl, ethoxymethyl etc.) or alkylthioalkyl (for example, methylthiomethyl, ethylthiomethyl etc.), and in case a plurality of substituents is present, they may be identical or different.

The "5- or 6-membered heterocyclic group" may be benzo-condensed and such a "benzo-condensed 5- or 6-membered heterocyclic group" includes the heterocyclic benzo-condensed groups mentioned above in conjunction with "5- or 6-membered aromatic heterocyclic group" and their specific examples include univalent groups derived from benzo[b]thiophene, benzothiazole, benzoimidazole, benzotriazole, quinoline etc. These condensed heterocyclic groups may also be substituted with, for example, cyano, nitro, halogen (for example, fluoro, chloro, bromo etc.), alkyl (for example, methyl, ethyl, n- or iso-propyl, n-, sec-, iso-, or tert-butyl etc.), alkoxy (for example, methoxy, ethoxy, n- or iso-propoxy etc.), alkylthio (for example, methylthio, ethylthio, n- or iso-propylthio etc.), alkoxyalkyl (for example, methoxymethyl, ethoxymethyl etc.) or alkylthioalkyl (for example, methylthiomethyl, ethylthiomethyl etc.), and in case a plurality of substituents is present, they may be identical or different.

Formula I provides a general definition of the isothiazolecarboxamides according to the invention. Preferred compounds of the forrnula (I) are those, in which X represents fluoro, chloro, bromo, methyl, ethyl or trifluoromethyl, Y represents a hydrogen atom, fluoro, chloro, bromo, cyano, methoxycarbonyl or ethoxycarbonyl, $R^1$, $R^2$ and $R^4$ each independently represents a hydrogen atom, methyl, ethyl, n-propyl or isopropyl, and $R^3$ represents a hydrogen atom, $C_{1-12}$ alkyl, $C_{3-6}$ cycloalkyl, $C_{2-6}$ alkenyl which may be substituted with phenyl, or $R^3$ represents $C_{5-6}$ cycloalkenyl, $C_7$ bicycloalkenyl, $C_{1-2}$ haloalkyl, substituted $C_{1-4}$ alkyl (substituents here are 1 or 2 groups selected from the group consisting of hydroxy, $C_{1-4}$ alkoxy, mercapto, $C_{1-4}$ alkylthio, $C_{1-4}$ alkylsulfinyl, $C_{1-4}$ alkylsulfonyl, phenyl and a 5-membered heterocyclic ring having 1–3 nitrogen atoms which may be benzo-condensed), or $R^3$ represents phenyl, which may be substituted with 1 to 4 groups selected from the group consisting of $C_{1-4}$ alkyl, halogen, $C_{1-4}$ haloalkyl, $C_{1-4}$ haloalkoxy, nitro, cyano, $C_{1-4}$ alkoxy, benzyloxy, phenoxy, $C_{1-4}$ alkylenedioxy, $C_{1-4}$ alkylthio, di-$C_{1-4}$ alkyl-amino and phenyl, or $R^3$ represents naphtyl, which may be substituted with methoxy, or $R^3$ represents a 5- or 6-membered heterocyclic group, which has 1 to 3 hetero-atoms selected from the group consisting of nitrogen, oxygen and sulfur, which heterocyclic groups may be benzo-condensed and may be substituted with 1 to 3 substituents selected from the group consisting of $C_{1-4}$ alkyl, halogen, $C_{1-4}$ alkoxy, $C_{1-4}$ alkylthio and nitro, or $R^2$ and $R^3$, together with the carbon atom to which they are bonded, form a $C_{1-6}$ cycloalkyl, which may be substituted with 1 or 2 methyl groups, or $R^2$ and $R^3$, together with the carbon atom to which they are bonded, form a 5- or 6-membered heterocyclic ring, which comprises one nitrogen atom and which may be substituted with 1 or 2 methyl groups, or $R^2$ and $R^3$, together with the carbon atom to which they are bonded, form a group of the formula

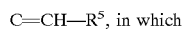

$C=CH-R^5$, in which $R^5$ represents a hydrogen atom, methyl or ethyl, or $R^3$ and $R^4$, together with the carbon atom and the carbonyl group to which they are bonded, form a 5- or 6-membered heterocyclic ring having one ring-constituting oxygen atom and being substituted with one oxo group, with the proviso, however, that $R^3$ does not represent isopropyl, if X and Y represent chloro, $R^1$ and $R^2$ represent hydrogen and $R^4$ represent methyl, ethyl, n-propyl or isopropyl.

Particularly preferred are the compounds of the formula (I), in which

X represents chloro or methyl,

Y represents a hydrogen atom, chloro or cyano, $R^1$ $R^2$ and $R^4$ each independently represents a hydrogen atom, methyl or ethyl, $R^3$ represents a hydrogen atom, $C_{1-12}$ alkyl, cyclopropyl, cyclohexyl, vinyl allyl, 1-propenyl, 1-methylvinyl, 2-methyl-1-propenyl, 1-pentenyl, 1-methyl-1-pentenyl, 1-n-butyl-vinyl, 2-phenyl-vinyl, 1-methyl-2-phenyl-vinyl, 3-cyclohexenyl, 5-norbornen-2-yl, chloromethyl, tirfluoromethyl, hydroxymethyl, 1-hydroxyethyl, methoxymethyl, mercaptomethyl, methylthiomethyl, methylthioethyl, methylsulfinylethyl, methylsulfonylmethyl, benzyl, α-methylbenzyl, phenethyl, 2-methylphenethyl, 4-imidazolylmethyl, 3-indolylmethyl, or $R^3$ represents phenyl, which may be substituted with 1 to 3 groups selected from the group consisting of methyl, ethyl, n-propyl, isopropyl, tert-butyl, fluoro, chloro, bromo, trifluoromethyl, trifluoromethoxy, cyano, methoxy, benzyloxy, phenoxy, methylenedioxy, methylthio, nitro, dimethylamino and phenyl, or $R^3$ represents 1-naphthyl, 2-napthyl, 2-methoxy-1-naphthyl, or $R^3$ represents a 5- or 6-membered heterocyclic group with 1 or 2 heteroatoms selected from nitrogen, oxygen and sulfur, which heterocyclic groups may be benzo-condensed and may be substituted with 1 to 3 substituents selected from methyl, chioro, bromo, methoxy, methylthio and nitro, or $R^2$ and $R^3$, together with the carbon atom to which they are bonded, form a group selected from cyclopentyl, cyclohexyl, 4,4-dimethyl-cyclohexyl, N-methylpiperidin-4-yl and vinylidene, or R³ and R⁴, together with the carbon atom and the carboxyl group to which they are bonded, form a 1-oxo-2-tetrahydrofuryl group, with the proviso, however, that R³ does not represent isopropyl, if X and Y represent chloro, R¹ and R² represent hydrogen and R⁴ represents methyl or ethyl.

If 3,4-dichloro-5-isothiazolecarbonyl chloride and methyl 2-amino-3-methylpentanoate are used as starting materials, process (a) according to the invention can be illustrated by the following formula scheme If N-(1-cyano-heptyl)-3,4-dichloro-5-isothiazolecarboxamide and methanol are used as starting materials, process (b) according to the invention can be illustrated by the following formula scheme.

If methyl 2-[(3,4-dichloro-5-isothiazolyl)-carboxamido]-propanoate is used as starting material and an aqueous solution of sodium hydroxide is used as reaction component, process (c) according to the invention can be illustrated by the following formula scheme.

Formula (II) provides a general definition of the isothiazolecarboxylic acid chlorides, which are required as starting materials for carrying out process (a) according to the invention. In this formula, X and Y preferably have those meanings, which have already been mentioned as preferred for these substituents.

The following compounds may be mentioned as examples of isothiazolecarboxylic acid chlorides of the formula (II):

3,4-dichloro-5-isothiazolecarbonyl chloride,
3-chloro-4-cyano-5-isothiazolecarbonyl chloride,
3-methyl-5-isothiazolecarbonyl chloride,
4-chloro-3-methyl-5-isothiazolecarbonyl chloride,
4-cyano-3-trifluoromethyl-5-isothiazolecarbonyl chloride,
3-chloro-4-methoxycarbonyl-5-isothiazolecarbonyl chloride etc.

The isothiazolecarboxylic acid chlorides of the formula (II) are known (see JP-A 59 024/1993). They can be prepared by reacting isothiazolecarboxylic acids of the formula (VI)

in which

X and Y have the above-mentioned meanings, with chlorinating agents, such as thionyl chlorides, phosphoryl chloride, phosphorous pentachloride etc.

Formula (III) provides a general definition of the amines, which are required as reaction components for carrying out process (a) according to the invention. In this formula, R¹, R², R³ and R⁴ preferably have those meanings, which have already been mentioned as preferred for these substituents.

The following compounds may be mentioned as examples of the amines of the formula (III), which may also be designated as amino acids or amino acid esters:

glycine,
glycine ethyl ester,
N-methylglycine ethyl ester,
alanine,
alanine methyl ester,
phenylalanine,
phenylalanine methyl ester,
cysteine ethyl ester,
serine methyl ester,
methyl 2-amino-2-(3-furyl)acetate etc.

The compounds of the formula (III) are known in the area of organic chemistry or can be prepared by known processes.

Formula (IV) provides a general definition of the isothiazolecarboxylic acid derivatives, which are required as starting materials of carrying out process (b) according to the invention. In this formula, X, Y, $R^1$, $R^2$ and $R^3$ preferably have those meanings, which have already been mentioned as preferred for these substituents.

The following compounds may be mentioned as examples of the isothiazolecarboxylic acid derivatives of the formula (IV):

N-cyanomethyl-3,4-dichloro-5-isothiazolecarboxamide,

N-cyanomethyl-N-methyl-3,4-dichloro-5-isothiazolecarboxamide,

N-(1-cyano-1,2-dimethylpropyl)-3,4-dichloro-5-isothiazolecarboxamide,

N-cyano-(3-furyl)-methyl-3,4-dichloro-5-isothiazolecarboxamide,

N-(1-cyanoheptyl)-3,4-dichloro-5-isothiazolecarboxamide,

N-(1-cyano-1,2-dimethylpropyl)-3-chloro-4-cyano-5-isothiazolecarboxamide,

N-(1-cyano-2-methoxyethyl)-3,4-dichloro-5-isothiazolecarboxamide,

N-(1-cyanocyclopentyl)-3,4-dichloro-5-isothiazolecarboxamide,

N-cyano-phenyl)-methyl-3,4-dichloro-5-isothiazolecarboxamide,

N-(1-cyano-2-methylpropyl)-3-methyl-4-chloro-5-isothiazolecarboxamide etc.

The isothiazolecarboxylic acid derivatives of the formula (IV) are partly novel and have not all been described in the literature so far.

The isothiazolecarboxylic acid derivatives of the formula (IV) can be prepared according to known processes, such as those which are described in JP-A 119 463/1988, JP-A 121 263/1989, JP-A 199 963/1989 and JP-A 149 572/1990.

Thus, isothiazolecarboxylic acid derivatives of the formula (IV) can be prepared by reacting isothiazolecarboxylic acid chlorides of the formula

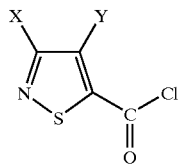

(II)

in which
X and Y have the above-mentioned meanings,
with amino derivatives of the formula

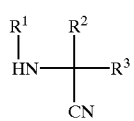

(VII)

in which
$R^1$, $R^2$ and $R^3$ have the above-mentioned meanings,
in the presence of an inert diluent and, if appropriate, in the presence of an acid binding agent.

The amino-derivative of the formula (VII) are known or can be prepared by known processes, such as the process described in "JIKKEN KAGAKU KOUZA" (lecture on experimental chemistry) $4^{th}$ edition, vol. 22 (Maruzen, 1992), pp. 193–195, or by Strecker's reaction.

The isothiazolecarboxylic acid derivatives of the formula (IV) have a fungicidal activity and can be used for the control of plant diseases.

Formula (V) provides a general definition of the compounds, which are required as reaction components for carrying out process (b) according to the invention. In this formula, $R^4$ preferably has those meanings, which have already been mentioned as preferred for this substituent.

The following compounds may be mentioned as examples of the compounds of the formula (V): water, methyl alcohol, ethyl alcohol, n-propyl alcohol, isopropyl alcohol, n-butyl alcohol, isobutyl alcohol, sec-butyl alcohol; tert-butyl alcohol etc.

The compounds of the formula (V) are known or can be prepared by known processes.

Formula (Ia) provides a general definition of the isothiazolecarboxamides, which are required as starting materials for carrying out process (c) according to the invention. In this formula, X, Y, $R^1$, $R^2$ and $R^3$ preferably have those meanings, which have already been mentioned as preferred for these substituents. M preferably represents methyl or ethyl.

The following compounds may be mentioned as examples of the isothiazole-carboxamides of the formula (Ia):

methyl 2-[(3,4-dichloro-5-isothiazolyl)-carboxamido] propionate, methyl 2-[(3,4-dichloro-5-isothiazolyl)-carboxamido]-2-methylpropionate, methyl 2-[(3,4-dichloro-5-isothiazolyl)-carboxamido]-3-methylbutyrate, ethyl 2-[(3,4-dichloro-5-isothiazolyl)-carboxamido]-2-methylpropionate etc.

The isothiazolecarboxamides of the formula (Ia) are compounds according to the invention, which can be prepared by process (a).

All inert organic solvents customary for such reactions can be used as diluents for carrying out process (a) according to the invention. Suitable solvents preferably include aliphatic alicyclic and aromatic hydrocarbons (which may optionally be chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM) etc.; ketones, for example, acetone, methyl ethyl ketone (MEK), methyl isopropyl ketone, methyl isobutyl ketone (MIBK) etc.; nitrites, for example, acetonitrile, propionitrile, acrylonitrile etc.; alcohols, for example, methanol, ethanol, isopropanol, butanol, ethylene glycol etc.; esters, for example, ethyl acetate, amyl acetate etc.; acid amides, for example, dimethylformarnide (DMF), dimethylacetamide (DMA), N-methylpyrrolidone, 1,3-dimethyl-2-imidazolidinone, hexamethylphosphoric triamide (HMPA) etc.; sulfones, sulfoxides, for example, dimethyl sulfoxide (DMSO), sulfolane etc.; and bases, for example, pyridine etc. Water can also be used as a diluent for carrying out process (a) according to the invention.

Suitable acid-binding agents for carrying out process (a) according to the invention are all customary inorganic and organic acid acceptors.

The following can preferably be used: inorganic bases such as hydrdes, hydroxides, carbonates, bicarbonates etc. of alkali metals and alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, calcium hydroxide etc.; inorganic alkali metal amides, for example, lithium amide, sodium amide, potassium amide etc.; and organic bases such as alcoholates, tertiary amines, dialkylaminoanilines and pyridines, for example, triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo-[5,4,0]undec-7-ene (DBU) etc.; organolithium compounds, for example, methyl lithium, n-butyl lithium, sec-butyl lithium, tert-butyl lithium, phenyl lithium, dimethyl copper lithium, lithium diisopropylamide, lithium cyclohexyl isopropylamide, lithium dicyclohexylamide, n-butyl lithiumADBACO, n-butyl lithiumADBU, n-butyl lithiumATMEDA etc.

Process (a) according to the invention can also be carried out in the presence of a phase-transfer catalyst.

As examples of diluents used in that case there may be mentioned water; aliphatic, alicyclic and aromatic hydrocarbons (which may optionally be chlorinated), for example, pentane, hexane, cyclohexane, petroleum ether, ligroine, benzene, toluene, xylene, dichloromethane, chlorobenzene, dichlorobenzene etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM) etc.; nitriles, for example, acetonitrile, propionitrile, acrilonitrile etc.

As examples of phase-transfer catalysts there may be mentioned quaternary ions, for example, tetramethylammonium bromide, tetrapropylammonium bromide, tetrabutylammonium bromide, tetrabutylammonium hydrogen sulfate, tetrabutylamnonium iodide, trioctylmethylammonium chloride, benzyltriethylanmmonium bromide, butylpyridinium bromide, heptylpyridinium bromide, benzyltriethylarnmonium chloride etc.; crown ethers, for example, dibenzo-18-crown-6, dicyclohexyl-18-crown-6, 18-crown-6 etc.; cryptands, for example, [2.2.2]-cryptate, [2.1.11]-cryptate, [2.2.1]-cryptate, [2.2.1]-cryptate, [3.2.2]-cryptate etc.

When carrying out process (a) according to the invention, the reaction temperatures can be varied within a substantially wide range. The reaction is generally carried out at a temperature between about −30° C. and about +150° C., preferably between about 0° C. and about 80° C.

Process (a) according to the invention is generally carried out-under atmospheric pressure but, if desired, can also be carried out under elevated or reduced pressure.

When carrying out process (a) according to the invention, in general 1 mole of an isothiazolecarboxylic acid chloride of the formula (II) is reacted with 1 to 1.2 moles of an amine of the formula (III) in the presence of 1 to 2 moles of an acid binding agent, such as triethylamine, and in the presence of a diluent, such as dichloromethane.

Process (b) according to the invention can also be carried out in the presence of a diluent. Suitable diluents are all customary inert organic solvents.

The following can preferably be used:aliphatic, alicyclic and aromatic hydrocarbons (which may optionally be chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene etc.; ethers, for example, ethyl ether, methyl ethyl ether, isopropyl ether, butyl ether, dioxane, dimethoxyethane (DME), tetrahydrofuran (THF), diethyleneglycol dimethyl ether (DGM) etc.; ketones, for example, acetone, methyl ethyl ketone (MEK), methyl isopropyl ketone, methyl isobutyl ketone (MIBK) etc.; nitriles, for example, acetonitrile, propionitrile, acrylonitrile etc.; esters, for example, ethyl acetate, amyl acetate etc.; acid amides, for example, dimethylformamide (DMF), dimethyliacetamide (DMA), N-methylpyrrolidone, 1,3-dimethyl-2-imidazolidinone, hexamethylphosphoric tniamide (HMPA) etc.; sulfones, sulfoxides, for example, dimethyl sulfoxide (DMSO), sulfolane etc.; and bases, for example, pyridine etc., Process (b) according to the invention can also be conducted in the presence of an acid catalyst. As examples of such acid catalysts there may be mentioned mineral acids, such as hydrochloric acid, hydrogen chloride gas, sulfuric acid, nitric acid, hydrobromic acid, sodium hydrogen sulfite etc.; organic acids, such as formic acid, acetic acid, trifluoroacetic acid, propionic acid, methanesulfonic acid, benezene-sulfonic acid, p-toluenesulfonic acid etc.; organic amine hydrochlorides, such as pyridine hydrochloride, triethylamine hydrochloride etc.; amine sulfonates, such as pyridine p-toluenesulfonate, triethylamine p-toluenesulfonate etc.

When carrying out process (b) according to the invention, the reaction temperatures can be varied within a substantially wide range. The reaction is generally carried out at a temperature between about −30° C. and about +150° C., preferably between about −10° C. and about +80° C.

Process (b) according to the invention is generally carried out under atmospheric pressure but, if desired, can also be carried out under elevated or reduced pressure.

When carrying out process (b) according to the invention, in general 1 mole of an isothiazolecarboxylic acid derivative of the formula (IV) is reacted with 1 to 1.5 moles of a compound of the formula (V) in the presence of 1 to 1.5 moles of an acid catalyst, such as hydrogen chloride gas, and in the presence of a diluent, such as diethyl ether.

Process (c) according to the invention can also be carried out in the presence of a diluent. Suitable diluents are all customary inert organic solvents. The following can preferably be used:aliphatic, alicyclic and aromatic hydrocarbons (which may optionally be chlorinated), for example, pentane, hexane, cyclohexane, petroleum ether, ligroine, benzene, toluene, xylene, dichloromethane, chloroform, carbon tetrachloride, 1,2-dichloroethane, chlorobenzene, dichlorobenzene etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM) etc.; ketones, for example, acetone, methyl ethyl ketone (MEK), methyl isopropyl ketone, methyl isobutyl ketone (MIBK) etc.; nitrites, for example, acetonitrile, propionitrile, acrylonitrile etc.; alcohols, for example, methanol, ethanol, isopropanol, butanol, ethylene glycol etc.; esters, for example, ethyl acetate, amyl acetate etc.; acid amides, for example, dimethylformamide (DMF), dimethyl-acetamide (DMA), N-methylpyrrolidone, 1,3-dimethyl-2-imidazolidinone, hexamethylphosphoric triamide (HMPA) etc.; sulfones, sulfoxides, for example, dimethyl sulfoxide (DMSO), sulfolane etc.; and bases, for example, pyridine etc. If an excess of water is employed, it may serve as reaction component as well as a diluent. Suitable acid-binding agents for carrying out process (c) according to the invention are all customary inorganic bases and strong organic bases. Preferred as inorganic bases are hydrides, hydroxides, carbonates, bicarbonates etc. of alkali metals and alkaline earth metals, for example, sodium hydride, lithium hydride, sodium hydrogen carbonate, potassium hydrogen carbonate, sodium carbonate, potassium carbonate, lithium hydroxide, sodium hydroxide, potassium hydroxide, calcium hydroxide etc.; and preferred organic bases are organolithium compounds, for example, methyl lithium, n-butyl lithium, sec-butyl lithium, tert-butyl lithium, phenyl lithium, dimethyl copper lithium, lithium diisopropylamide, lithium cyclohexyl isopropylamide, lithium dicyclohexylamide, n-butyl lithiumADBACO, n-butyl lithiumADBU, n-butyl lithiumATMEDA etc.

Suitable acid catalysts for carrying out process (c) according to the invention are mineral acids, for example, hydrochloric acid, sulfuric acid, nitric acid, hydrobromic acid, sodium hydrogen sulfite etc.; organic acids, for example, formic acid, acetic acid, trifluoroacetic acid, propionic acid, methane sulfonic acid, benezene sulfonic acid, p-toluene sulfonic acid etc.; organic amine hydrochlorides, for example, pyridine hydrochloride, triethylamine hydrochloride etc.; amine sulfonates, for example, pyridine p-toluenesulfonate, triethylamine p-toluenesulfonate etc.

Process (c) according to the invention can also be carried out in the presence of a phase-transfer catalyst. As examples of diluents used in that case there may be mentioned aliphatic, alicyclic and aromatic hydrocarbons (which may optionally be chlorinated), for example, pentane, hexane, cyclohexane, petroleum ether, ligroine, benzene, toluene, xylene, dichloromethane, chlorobenzene, dichlorobenzene etc.; ethers, for example, ethyl ether, methyl ethyl ether, isopropyl ether, butyl ether, dioxane, dimethoxyethane (DME), tetrahydrofuran (THF), diethylene glycol dimethyl ether (DGM) etc.; nitriles, for example, acetonitrile, propionitrile, acrilonitrile etc.

As examples of phase-transfer catalysts there may be mentioned quaternary ions, for example, tetramethylammonium bromide, tetrapropylanrmonium bromide, tetrabutylammonium bromide, tetrabutylammonium hydrogen sulfate, tetrabutylammonium iodide, trioctylmethylammonium chloride, benzyltriethylammonium bromide, butylpyridinium bromide, heptylpyridinium bromide, benzyltriethylammonium chloride etc.; crown ethers, for example, dibenzo-18-crown-6, dicyclohexyl-18-crown-6, 18-crown-6 etc.; cryptands, for example, [2.2.2]-cryptate, [2.1.1]-cryptate, [2.2.1]-cryptate, [2.2.B]-cryptate, [3.2.2]-cryptate etc.

When carrying out process (c) according to the invention, the reaction temperatures can also be varied within a substantially wide range. The reaction is generally carried out at a temperature between about −30° C. and about +150° C., preferably between about 0° C. and about 80° C.

Process (c) according to the invention is generally carried out under atmospheric pressure but, if desired, can also be carried out under elevated or reduced pressure.

When carrying out process (c) according to the invention, in general 1 mole of an isothiazolecarboxamide of the formula (Ia) is reacted with an excess of water in the presence of a base, such as an aqueous solution of sodium hydroxide (~10%), in the presence of a diluent, such as methanol.

The isothiazolecarboxamides according to the present invention exhibit a strong microbicidal activity. Thus, they can be used for combating undesired microorganisms, such as phytopathogenic fungi and bacteriae, in agriculture and horticulture. The compounds are suitable for the direct control of undesired microorganisms as well as for generating resistance in plants against attack by undesirable plant pathogens.

Resistance-inducing substances in the present context are to be understood as those substances which are capable of stimulating the defence system of plants such that the treated plants, when subsequently inoculated with undesirable microorganisms, display substantial resistance to these microorganisms.

Undesirable microorganisms in the present case are to be understood as phytopathogenic fungi and bacteriae. The substances according to the invention can thus be employed to generate resistance in plants against attack by the harmfiul organisms mentioned within a certain period of time after the treatment. The period of time within which resistance is brought about in general extends from 1 to 10 days, preferably 1 to 7 days, after treatment of theplants with the active compounds.

Generally, the compounds according to the invention can be used as fulngicides for combating phytopathogenic fulngi, such as Plasmodiophoromycetes, Oomycetes, Chytridiomycetes, Zygomycetes, Ascomycetes, Basidiomyceptes and Deuteromycetes, and can also be used as bactericides for combating bacteriae, such as Pseudomonoadaceae, Rhizobiacean , Enterobacterfiactae, Corynebacteriacean and Streptomycetaceae.

The compounds according to the present invention are particularly suitable for causing resistance against infection of plants by plant pathogens, such as Pyricularia oryzae, Phythophthora infestans etc.

The good toleration, by plants, of the active compounds, at the concentrations required for combating plants diseases, permits treatment of above-ground parts of plants, of vegetative propagation stock and seeds, and of the soil.

The compounds according to the present invention have a low toxicity against warmblooded animals and therefore can be used safely.

The active compounds can be converted into the customary formulations, such as solutions, emulsions, wettable powders, suspensions, powders, foams, pastes, granules, tablets, aerosols, natural and synthetic materials impregnated with active compound, very fine capsules in polymeric substances, coating compositions for use on seed, and formlations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl-isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolings, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used nonionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 per cent by weight of active compound, preferably from 0.5 to 90 per cent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

In many cases, synergistic effects are achieved, i.e. the activity of the mixture exceeds the activity of the individual components.

Examples of co-components in mixtures are the following compounds:
Fungicides:
 aldimorph, ampropylfos, ampropylfos potassium, andoprim, anilazine, azaconazole, azoxystrobin,
 benalaxyl, benodanil, benomyl, benzamacrin, benzamacril-isobutyl, bialaphos, binapacryl, biphenyl, bitertanol, blasticidin-S, bromuconazole, bupirimate, buthiobate,
 calcium polysulphide, capsimycin, captafol, captan, carbendazim, carboxin, carvon, quinomethionate, chlobenthiazone, chlorfenazole, chloroneb, chloropicrin, chloro-thalonil, chlozolinate, clozylacon, cufraneb, cymoxanil, cyproconazole, cyprodinil, cyprofuram,
 debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemoiph, dodine, drazoxolon,
 edifenphos, epoxiconazole, etaconazole, ethirimol, etridiazole,
 famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as:copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dirnethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
quinconazole, quintozene (PCNB), quinoxyfen,
sulphur and sulphur preparations,
tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide, isopropyl {2-methyl-1-[[[1(4-methylphenyl)-ethyl]-amino]-carbonyl]-propyl}-carbamate,
1-(2,4-dichlorophenyl)-2-(1H-1,2,4-triazol-1-yl)-ethanone O-(phenylrnethyl)-oxime,
1-(2-methyl-1-naphthalenyl)-1H-pyrrol-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole, 1-[1-[2-[(2,4-dichlorophenyl)-methoxyl]-phenyl]-ethenyl]-1H-imidazole,
1methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranlosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano[(1-methyl-2-propinyl)-oxy]-methyl]-benzamide,
3-(1,1dimethylpropyl-1oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy] 2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholinehydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-fornyl-N-hydroxy-DL-alanine-sodium salt,
O,O-diethyl[2-(dipropylamino)-2-oxoethyl-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
Bactericides:
bronopol, dichlorophen, nitrapyrin, nickel dimethylditbiocarbamate, kasugamycin, octhilinone, furancarboxylic acid, oxytetracyclin, probenazole, streptomycin, tecloftalam, copper sulpbate and other copper preparations.
Insecticides/acaricides/nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
Bacillus popilliae, Bacillus sphaericus, Bacillus subtilis, Bacillus thuringiensis, baculoviruses, Beauveria bassiana, Beauveria tenella, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispernethrin, clocythrin, cloethocarb, clofentezine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoat, dimethylvinphos, diofenolan, disulfoton, docusat-sodium, dofenapyn,
eflusilanate, emamectin, empenthrin, endosulfan, Entomopfthora spp., esfenvalerate, ethiofencarb, ethion, ethoprophos, etofenprox, etoxazole, etrimphos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexanumuron, hexythiazox, hydroprene, imidacloprid, isazophos, isofenphos, isoxathion, ivermectin, lambda-cyhalothrin, lufenuron, malathion, mecarbam, metaldehyde, methamidophos, Metharhizium anisopliae, Metharhizium flavoviride, methidathion, methiocarb, methomyl, methoxyfenozide, metolcarb, metoxadiazone, mevinphos, milbemectin, monocrotophos, naled, nitenpyrarn, nithiazine, novaluron, nuclear polyhedrosis viruses, omethoat, oxamyl, oxydemethon M, Paecilomyces fumosoroseus, parathion A, parathion M, pennethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, tichlophenidine, trichlorfon, triflumuron, trimethacarb, vamidothion, vaniliprole, Verticillium lecanii,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]2,2-dimethylcyclopropanecarboxylate, (3-phenoxyphenyl)-methyl 2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone, Bacillus thuringiensis strain EG-2348,

[2-benzoyl-1-(1,1dimethylethyl)-hydrazinobenzoic acid, 2,2-dimethyl-3-(2,4-dichlorophenyl)-2-oxo-1-oxaspiro [4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-pheny]-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

The active compounds can be used as such or in the form of their formulations or the use forms prepared therefrom by further dilution, such as ready-to-use solutions, emulsions, suspensions, powders, tablets, pastes, microcapsules and granules. They are used in the customary manner, for example by watering, immersion, spraying, atomising, misting, vaporizing, injecting, forming a slurry, brushing on, dusting, scattering, dry dressing, moist dressing, wet dressing, slurry dressing or encrusting.

In the treatment of parts of plants, the active compounds concentration in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed.

The preparation and use. of the active compounds according to the invention can be seen fromt he following examples.

SYNTHESIS EXAMPLE 1

(Compound No. 22)

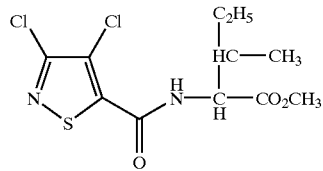

Process (a):

After thionyl chloride (10 ml) had been added to 3,4-dichloro-5-isothiazole-carboxylic acid (0.99 g), the mixture was refluxed by heating for 2 hours. The excess of thionylchloride was then distilled off under reduced pressure, and 3,4-dichloro-5-isothiazolecarboxylic acid chloride was obtained.

Methyl (2S,3S)-(+)-2-amino-3-methylpentanoate hydrochloride (0.91 g) and triethylamine (1.06 g) were suspended in 1,2-dichloroethane (40 ml) and stirred at room temperature for 2 hours. The mixture was then cooled down to a temperature lower than 4° C., and then a solution of the above-mentioned 3,4-dichloro-5-isothiazolecarboxylic acid chloride in 1,2-dichloroethane (10 ml) was added drop by drop. After stirring at room temperature for 4 hours, the reaction mixture was washed with a saturated solution of sodium bicarbonate in water and was then dried over anhydrous sodium sulfate. After the solvent had been distilled off under reduced pressure, the residue was purified by silica gel column chromatography (eluent: dichloromethane/ethanol=99/1) to obtain methyl 2-[3,4-dichloro-5-isothiazolyl)-carboxamido]-3-methylpentanoate (1.1 g) as an oily substance. ($n^D_{20}$ 1.5310)

SYNTHESIS EXAMPLE 2

(Compound No. 9)

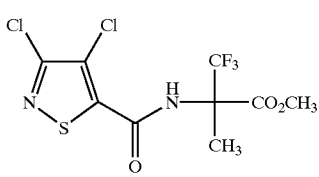

Process (a):

After thionyl chloride (10 ml) had been added to 3,4-dichloro-5-isothiazole-carboxylic acid (1.28 g), the mixture was refluxed by heating for 2 hours. The excess of thionyl-chloride was then distilled off under reduced pressure, and 3,4-dichloro-5-isothiazolecarboxylic acid chloride was obtained.

A solution of the above-mentioned 3,4-dichloro-5-isothiazolecarboxylic acid chloride in dehydrated 1,2-dichloroethane (10 ml) was added drop by drop to a solution of methyl 2-amino-3-trifluoromethyl-2-methylpropanoate (1.11 g) and triethylamine (0.72 g) in dehydrated 1,2-dichloroethane (30 ml) at a temperature lower than 4° C. After stirring at room temperature for 6 hours, the reaction mixture was washed with a saturated solution of sodium bicarbonate in water and was then dried over anhydrous sodium sulfate. After the solvent had been distilled off under reduced pressure, the residue was purified by silica gel column chromatography (eluent: dichloromethane/ethanol=99/1) to obtain methyl 2-[(3,4-dichloro-5-isothiazolyl)-carboxamido]-3-trifluoromethyl-2-methylpropanoate (1.2 g) as an oily substance. ($n^D_{20}$ 1.5005)

SYNTHESIS EXAMPLE 3

(Compound No. 30)

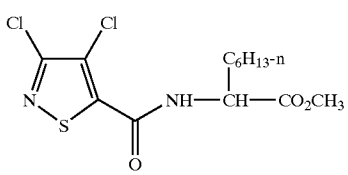

Process (b):

A solution of N-(1-cyanoheptyl)-3,4-dichloro-5-isothiazolecarboxamide (1.1 g) in dehydrated methanol (10 ml) was saturated with hydrogen chloride under ice cooling and left standing overncight. Ethylacetate and water were added to the reaction mixture, and the organic phase was separated. This organic phase was washed with a saturated solution of sodium bicarbonate in water. Then it was washed with water and dried with magnesium sulfate. After the solvent had been distilled off under reduced pressure, the obtained residue was purified by silica gel column chromato-graphy (eluent: dichloromethane) to obtain methyl 2-[(3,4-dichloro-5-isothiazolyl)-carboxamide]-heptanoate (0.6 g) as an oily substance. ($n^D_{20}$ 1.5280)

SYNTHESIS EXAMPLE 4

(Compound No. 13)

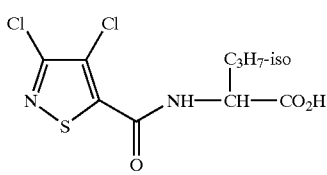

Process (c):

To a solution of methyl 2-[(3,4-dichloro-5-isothiazolyl)-carboxamido]-3-methyl-butyrate (1.5 g) in methanol (5 ml) a 10% aqueous solution of sodium hydroxide (10 ml) was added, and the resulting mixture was stirred at room temperature for 8 hours. After the reaction had been completed, methanol was distilled off under reduced pressure. By adding water and then concentrated hydrochloric acid to the residue, it was acidified and the mixture was extracted with ether. The ether phase was washed with a saturated sodium chloride solution in water and dried over magnesium sulfate. After that, ether was distilled off and the obtained crystals were washed with hexane to obtain 2-[(3,4-dichloro-5-isothiazolyl)-carboxamido]-3-methylbutyric acid (0.9 g). (mp 137–143° C.)

The following Table 1 shows the compounds, the syntheses of which were disclosed the Synthesis Examples 1 to 4, and other compounds, which can be synthesized in same manner.

TABLE 1

(I)

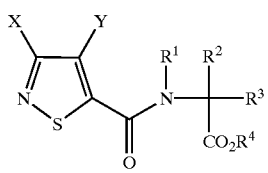

| Compound No. | X | Y | $R^1$ | $R^2$ | $R^3$ | $R^4$ | Physical Properties |
|---|---|---|---|---|---|---|---|
| 1 | Cl | Cl | H | H | H | $C_2H_5$ | mp 100–101° C. |
| 2 | Cl | CN | H | H | H | $CH_3$ | mp 98–99° C. |

TABLE 1-continued (I)

| Compound No. | X | Y | R¹ | R² | R³ | R⁴ | Physical Properties |
|---|---|---|---|---|---|---|---|
| 3 | Cl | Cl | CH$_3$ | H | H | C$_2$H$_5$ | (n$^D_{20}$ 1.5429) |
| 4 | Cl | Cl | H | H | CH$_3$ | CH$_3$ | mp 100–101° C. |
| 5 | Cl | Cl | H | H | CH$_3$ | H | mp 151–157° C. |
| 6 | Cl | CN | H | H | CH$_3$ | CH$_3$ | mp 100–101° C. |
| 7 | Cl | Cl | H | CH$_3$ | CH$_3$ | CH$_3$ | mp 86–87° C. |
| 8 | Cl | Cl | H | CH$_3$ | CH$_3$ | H | mp 170–171° C. |
| 9 | Cl | Cl | H | CH$_3$ | CF$_3$ | C$_2$H$_5$ | (n$^D_{20}$ 1.5005) |
| 10 | Cl | Cl | H | | CH$_2$ | CH$_3$ | mp 123–124° C. |
| 11 | Cl | Cl | H | H | C$_2$H$_5$ | CH$_3$ | |
| 12 | Cl | Cl | H | H | C$_3$H$_7$-n | CH$_3$ | |
| 13 | Cl | Cl | H | H | C$_3$H$_7$-iso | H | mp 137–143° C. |
| 14 | Cl | CN | H | H | C$_3$H$_7$-iso | CH$_3$ | mp 103–105° C. |
| 15 | CF$_3$ | CN | H | H | C$_3$H$_7$-iso | CH$_3$ | |
| 16 | CH$_3$ | Cl | H | H | C$_3$H$_7$-iso | CH$_3$ | (n$^D_{20}$ (1.5255) |
| 17 | CH$_3$ | H | H | H | C$_3$H$_7$-iso | CH$_3$ | |
| 18 | Cl | Cl | H | H | (cyclopropyl) | CH$_3$ | |
| 19 | Cl | Cl | H | H | C$_4$H$_9$-n | CH$_3$ | |
| 20 | Cl | Cl | H | H | C$_4$H$_9$-iso | CH$_3$ | (n$^D_{20}$ 1.5323) |
| 21 | CH$_3$ | Cl | H | H | C$_4$H$_9$-iso | CH$_3$ | (n$^D_{20}$ 1.5223) |
| 22 | Cl | Cl | H | H | C$_4$H$_9$-sec | CH$_3$ | (n$^D_{20}$ 1.5310) |
| 23 | CH$_3$ | Cl | H | H | C$_4$H$_9$-sec | CH$_3$ | (n$^D_{20}$ 1.5212) |
| 24 | Cl | Cl | H | H | C$_4$H$_9$-tert | CH$_3$ | |
| 25 | Cl | Cl | H | H | C$_5$H$_{11}$-n | CH$_3$ | |
| 26 | Cl | Cl | H | H | C$_5$H$_{11}$-iso | CH$_3$ | |
| 27 | Cl | Cl | H | H | C$_5$H$_{11}$-sec | CH$_3$ | |
| 28 | Cl | Cl | H | H | C$_5$H$_{11}$-tert | CH$_3$ | |
| 29 | Cl | Cl | H | H | C$_5$H$_{11}$-neo | CH$_3$ | |
| 30 | Cl | Cl | H | H | C$_6$H$_{13}$-n | CH$_3$ | (n$^D_{20}$ 1.5230) |
| 31 | Cl | Cl | H | H | C$_6$H$_{13}$-n | H | |
| 32 | Cl | Cl | H | H | CH$_2$Cl | CH$_3$ | mp 94–96° C. |
| 33 | Cl | Cl | H | H | CH$_2$OH | CH$_3$ | mp 115–120° C. |
| 34 | Cl | Cl | H | CH$_3$ | CH$_2$OH | CH$_3$ | mp 89–90° C. |
| 35 | CH$_3$ | Cl | H | H | CH$_2$OH | CH$_3$ | mp 108–112° C. |
| 36 | Cl | CN | H | H | CH$_2$OH | CH$_3$ | |
| 37 | Cl | Cl | H | H | CH$_2$OCH$_3$ | CH$_3$ | |
| 38 | Cl | Cl | H | H | CH$_2$SH | C$_2$H$_5$ | mp 133–136° C. |
| 39 | Cl | Cl | H | H | CH(OH)CH$_3$ | CH$_3$ | mp 89–92° C. |
| 40 | Cl | Cl | H | H | CH$_2$CH$_2$SCH$_3$ | CH$_3$ | (n$^D_{20}$ 1.5638) |
| 41 | Cl | Cl | H | H | CH$_3$CH$_2$S(O)CH$_3$ | CH$_3$ | |
| 42 | Cl | Cl | H | H | CH$_3$CH$_2$S(O)$_2$CH$_3$ | CH$_3$ | |
| 43 | CH$_3$ | Cl | H | H | CH$_2$CH$_2$SCH$_3$ | CH$_3$ | (n$^D_{20}$ 1.5549) |
| 44 | Cl | Cl | H | H | CH=CH$_2$ | CH$_3$ | |
| 45 | Cl | Cl | H | H | C(CH$_3$)=CH$_2$ | CH$_3$ | |
| 46 | Cl | Cl | H | H | C(CH$_3$)=CHC$_3$H$_7$-n | CH$_3$ | |
| 47 | Cl | Cl | H | H | C(C$_4$H$_9$-n)=CH$_2$ | CH$_3$ | |
| 48 | Cl | Cl | H | H | CH=CHCH$_3$ | CH$_3$ | |
| 49 | Cl | Cl | H | H | C$_9$H$_{19}$-n | CH$_3$ | |
| 50 | Cl | Cl | H | H | C$_{12}$H$_{23}$-n | CH$_3$ | |
| 51 | Cl | Cl | H | H | CH=CHC$_3$H$_7$-n | CH$_3$ | |
| 52 | Cl | Cl | H | H | CH=C(CH$_3$)$_2$ | CH$_3$ | |
| 53 | Cl | Cl | H | H | (cyclohexenyl) | CH$_3$ | |
| 54 | Cl | Cl | H | H | (norbornenyl) | CH$_3$ | |

TABLE 1-continued (I)

| Compound No. | X | Y | R¹ | R² | R³ | R⁴ | Physical Properties |
|---|---|---|---|---|---|---|---|
| 55 | Cl | Cl | H | H | CH₂–C₆H₅ (benzyl) | CH₃ | mp 74–75° C. |
| 56 | Cl | Cl | H | H | CH(CH₃)–C₆H₅ | CH₃ | |
| 57 | Cl | Cl | H | H | CH₂CH₂–C₆H₅ | CH₃ | |
| 58 | Cl | Cl | H | H | CH₂–CH(CH₃)–C₆H₅ | CH₃ | |
| 59 | Cl | Cl | H | H | CH=CH–C₆H₅ | CH₃ | |
| 60 | Cl | Cl | H | H | C(CH₃)–CH–C₆H₅ | CH₃ | |
| 61 | Cl | Cl | H | H | 1-methylnaphthyl | CH₃ | |
| 62 | Cl | Cl | H | H | 3-methylnaphthyl | CH₃ | |
| 63 | Cl | Cl | H | H | 1-methyl-2-methoxynaphthyl | CH₃ | |
| 64 | Cl | Cl | H | H | 4-methylphenyl (p-tolyl) | CH₃ | mp 152° C. |
| 65 | Cl | Cl | H | H | 4-methylphenyl | C₂H₅ | |

TABLE 1-continued
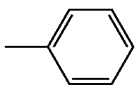
(I)
| Compound No. | X | Y | R¹ | R² | R³ | R⁴ | Physical Properties |
|---|---|---|---|---|---|---|---|
| 66 | Cl | Cl | $C_2H_5$ | H | 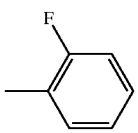 | $CH_3$ | |
| 67 | Cl | Cl | H | H |  | $CH_3$ | |
| 68 | Cl | Cl | H | H | 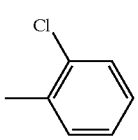 | $CH_3$ | mp 108–110° C. |
| 69 | Cl | Cl | H | H | 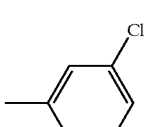 | $C_2H_5$ | |
| 70 | Cl | Cl | H | H | 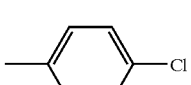 | $C_2H_5$ | |
| 71 | Cl | Cl | H | H | 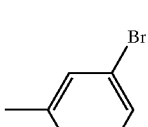 | $C_2H_5$ | |
| 72 | Cl | Cl | H | H | 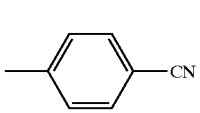 | $C_2H_5$ | |
| 73 | Cl | Cl | H | H | 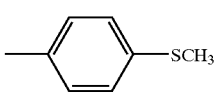 | $C_2H_5$ | |
| 74 | Cl | Cl | H | H | 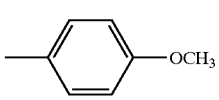 | $C_2H_5$ | |
| 75 | Cl | Cl | H | H | 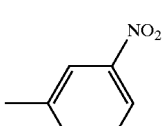 | $C_2H_5$ | |
| 76 | Cl | Cl | H | H | | $C_2H_5$ | |

TABLE 1-continued
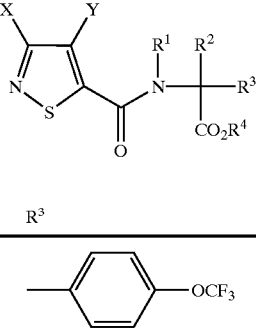
(I)
| Compound No. | X | Y | R¹ | R² | R³ | R⁴ | Physical Properties |
|---|---|---|---|---|---|---|---|
| 77 | Cl | Cl | H | H | 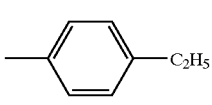 —OCF₃ | $C_2H_5$ | |
| 78 | Cl | Cl | H | H | 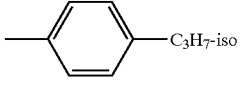 —C₂H₅ | $C_2H_5$ | |
| 79 | Cl | Cl | H | H | 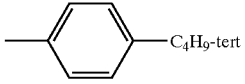 —C₃H₇-iso | $C_2H_5$ | |
| 80 | Cl | Cl | H | H | 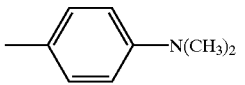 —C₄H₉-tert | $C_2H_5$ | |
| 81 | Cl | Cl | H | H | 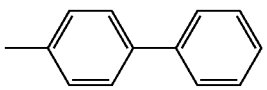 —N(CH₃)₂ | $C_2H_5$ | |
| 82 | Cl | Cl | H | H | 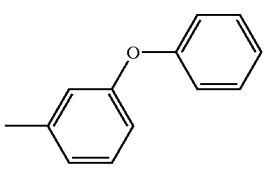 | $C_2H_5$ | |
| 83 | Cl | Cl | H | H | 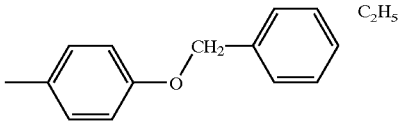 | $C_2H_5$ | |
| 84 | Cl | Cl | H | H | 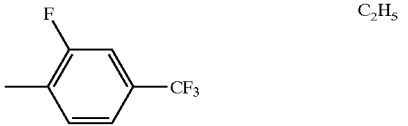 | $C_2H_5$ | |
| 85 | Cl | Cl | H | H | 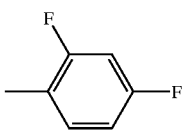 | $C_2H_5$ | |
| 86 | Cl | Cl | H | H | 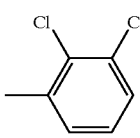 | $C_2H_5$ | |
| 87 | Cl | Cl | H | H |  | $C_2H_5$ | |

TABLE 1-continued
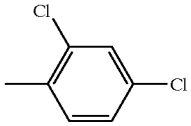
(I)
| Compound No. | X | Y | R¹ | R² | R³ | R⁴ | Physical Properties |
|---|---|---|---|---|---|---|---|
| 88 | Cl | Cl | H | H | 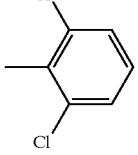 | $C_2H_5$ | |
| 89 | Cl | Cl | H | H | 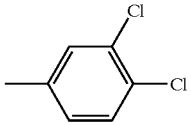 | $C_2H_5$ | |
| 90 | Cl | Cl | H | H |  | $C_2H_5$ | |
| 91 | Cl | Cl | H | H | 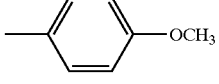 | $C_2H_5$ | |
| 92 | Cl | Cl | H | H | 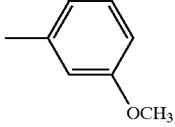 | $C_2H_5$ | |
| 93 | Cl | Cl | H | H | 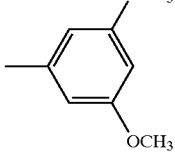 | $C_2H_5$ | |
| 94 | Cl | Cl | H | H | 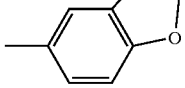 | $C_2H_5$ | |
| 95 | Cl | Cl | H | H |  | $C_2H_5$ | |

TABLE 1-continued
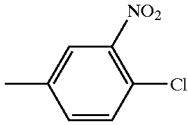
(I)
| Compound No. | X | Y | R¹ | R² | R³ | R⁴ | Physical Properties |
|---|---|---|---|---|---|---|---|
| 96 | Cl | Cl | H | H | 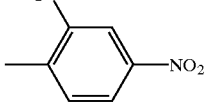 | $C_2H_5$ | |
| 97 | Cl | Cl | H | H | 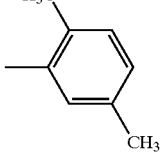 | $C_2H_5$ | |
| 98 | Cl | Cl | H | H | 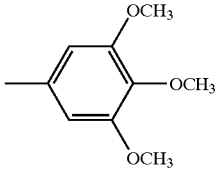 | $C_2H_5$ | |
| 99 | Cl | Cl | H | H | 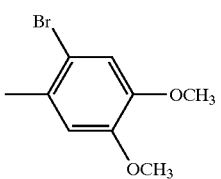 | $C_2H_5$ | |
| 100 | Cl | Cl | H | H | 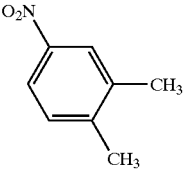 | $C_2H_5$ | |
| 101 | Cl | Cl | H | H | 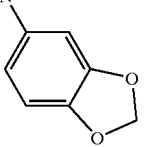 | $C_2H_5$ | |
| 102 | Cl | Cl | H | H | | $C_2H_5$ | |

TABLE 1-continued
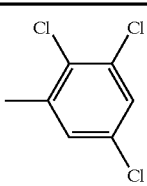
(I)
| Compound No. | X | Y | R¹ | R² | R³ | R⁴ | Physical Properties |
|---|---|---|---|---|---|---|---|
| 103 | Cl | Cl | H | H | 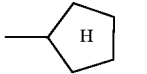 | $C_2H_5$ | |
| 104 | Cl | Cl | H | | 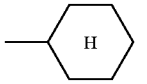 | $C_2H_5$ | |
| 105 | Cl | Cl | H | | 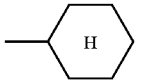 | $C_2H_5$ | |
| 106 | Cl | Cl | H | H | 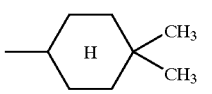 | H | |
| 107 | Cl | Cl | H | H | 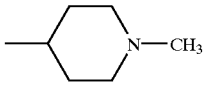 | $C_2H_5$ | |
| 108 | Cl | Cl | H | H | 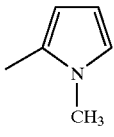 | $CH_3$ | |
| 109 | Cl | Cl | H | H | 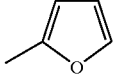 | $CH_3$ | |
| 110 | Cl | Cl | H | H | 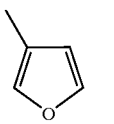 | $CH_3$ | |
| 111 | Cl | Cl | H | H |  | $CH_3$ | mp 71–73° C. |
| 112 | Cl | Cl | H | H | 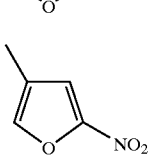 | $CH_3$ | |
| 113 | Cl | Cl | H | H |  | $C_2H_5$ | |

TABLE 1-continued
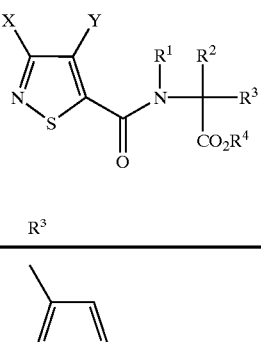
(I)
| Compound No. | X | Y | R¹ | R² | R³ | R⁴ | Physical Properties |
|---|---|---|---|---|---|---|---|
| 114 | Cl | Cl | H | H | 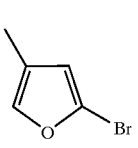 | $C_2H_5$ | |
| 115 | Cl | Cl | H | H | 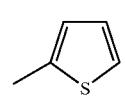 | $C_2H_5$ | |
| 116 | Cl | Cl | H | H | 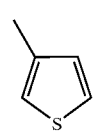 | $C_2H_5$ | |
| 117 | Cl | Cl | H | H | 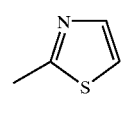 | $C_2H_5$ | |
| 118 | Cl | Cl | H | H | 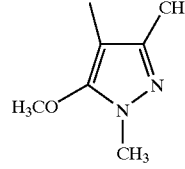 | $C_2H_5$ | |
| 119 | Cl | Cl | H | H | 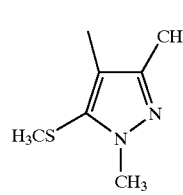 | $C_2H_5$ | |
| 120 | Cl | Cl | H | H | 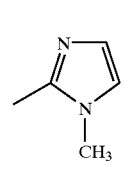 | $C_2H_5$ | |
| 121 | Cl | Cl | H | H | 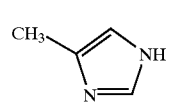 | $C_2H_5$ | |
| 122 | Cl | Cl | H | H | 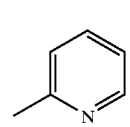 | $CH_3$ | |
| 123 | Cl | Cl | H | H |  | $C_2H_5$ | |

TABLE 1-continued

Structure (I):

$$\text{X-Y-isothiazole-C(=O)-N(R}^1\text{)-C(R}^2\text{)(R}^3\text{)-CO}_2\text{R}^4$$

| Compound No. | X | Y | R¹ | R² | R³ | R⁴ | Physical Properties |
|---|---|---|---|---|---|---|---|
| 124 | Cl | Cl | H | H | 3-pyridyl | $C_2H_5$ | |
| 125 | Cl | Cl | H | H | 3-pyridyl (isomer) | $C_2H_5$ | |
| 126 | Cl | Cl | H | H | 6-methyl-2-pyridyl | $C_2H_5$ | |
| 127 | Cl | Cl | H | H | indol-3-ylmethyl | $CH_3$ | mp 65–70° C. |
| 128 | Cl | Cl | H | H | quinolin-2-yl | $C_2H_5$ | |
| 129 | Cl | Cl | H | H | 4-methylquinolin-2-yl | $C_2H_5$ | |
| 130 | Cl | Cl | H | H | 2-oxotetrahydrofuran-3-yl | | mp 187–188° C. |

Preparation of isothiazolecarboxylic acid derivatives of the formula (IV).

SYNTHESIS EXAMPLE 5

(Compound No. IV-6)

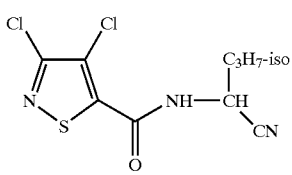

A solution of 3,4-dichloro-5-isothiazolecarboxylic acid chloride (2.1 g) in dichloro-methane (5 ml) was added drop by drop to a solution of 2-amino-3-methyl-butyronitrile (1.2 g) and triethylamine (1.5 g) in dichloromethane (10 ml) under ice cooling. After the addition was completed, the temperature was brought to room temperature, and the mixture was stirred for further 4 hours. The reaction mixture was then washed with water and dried over magnesium sulfate. The solvent was distilled off under reduced pressure and the remaining residue was purified by silica gel column chromatography (eluent: chloroformn) to obtain N-(1-cyano-2-methyl-propyl)-3,4-dichloro-5-isothiazolecarboxamide (1.5 g) (mp 120–121° C.).

The following Table 2 shows the compound, the synthesis of which was disclosed in Synthesis Example 5, and other compounds, which can be synthesized in the same manner.

TABLE 2

(IV)

| Compound No. | X | Y | R¹ | R² | R³ | Physical Properties |
|---|---|---|---|---|---|---|
| IV-1 | Cl | Cl | H | H | H | mp 134–135° C. |
| IV-2 | Cl | Cl | CH₃ | H | H | $n^D_{20}$ 1.5754 |
| IV-3 | Cl | Cl | H | H | CH₃ | |
| IV-4 | Cl | Cl | H | H | C₂H₅ | mp 65–66° C. |
| IV-5 | Cl | Cl | H | H | C₃H₇-n | mp 80–81° C. |
| IV-6 | Cl | Cl | H | H | C₃H₇-iso | |
| IV-7 | Cl | Cl | H | CH₃ | C₃H₇-iso | mp 104° C. |
| IV-8 | Cl | CN | H | CH₃ | C₃H₇-iso | mp 100–102° C. |
| IV-9 | Cl | Cl | H | H | 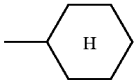 | |
| IV-10 | Cl | Cl | H | H | C₄H₉-n | |
| IV-11 | Cl | Cl | H | H | C₄H₉-iso | |
| IV-12 | Cl | Cl | H | H | C₄H₉-tert | |
| IV-13 | Cl | Cl | H | H | C₅H₁₁-n | |
| IV-14 | Cl | Cl | H | H | C₅H₁₁-iso | |
| IV-15 | Cl | Cl | H | H | C₅H₁₁-sec | |
| IV-16 | Cl | Cl | H | H | C₅H₁₁-tert | |
| IV-17 | Cl | Cl | H | H | C₅H₁₁-neo | |
| IV-18 | Cl | Cl | H | H | C₅H₁₁-n | $n^D_{20}$ 1.5249 |
| IV-19 | Cl | Cl | H | H | 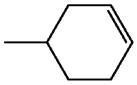 | |
| IV-20 | Cl | Cl | H | H | CH₂OCH₃ | mp 53–56° C. |
| IV-21 | Cl | Cl | H | H | CH₂SCH₃ | |
| IV-22 | Cl | Cl | H | CH=CH₂ | | |
| IV-23 | Cl | Cl | H | H | C(CH₃)=CH₂ | |
| IV-24 | Cl | Cl | H | H | C(CH₃)=CHC₃H₇-n | |
| IV-25 | Cl | Cl | H | H | C(C₄H₉-n)=CH₂ | |
| IV-26 | Cl | Cl | H | H | CH=CHCH₃ | |
| IV-27 | Cl | Cl | H | H | CH=CHC₃H₇-n | |
| IV-28 | Cl | Cl | H | H | CH=C(CH₃)₂ | |
| IV-29 | Cl | Cl | H | H |  | |
| IV-30 | Cl | Cl | H | H | 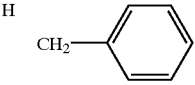 | |
| IV-31 | Cl | Cl | H | H | 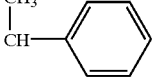 | |
| IV-32 | Cl | Cl | H | H | 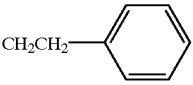 | |
| IV-33 | Cl | Cl | H | H |  | |

TABLE 2-continued (IV) Structure: isothiazole with X, Y substituents and C(=O)-N(R¹)-C(R²)(R³)(CN) group

| Compound No. | X | Y | R¹ | R² | R³ | Physical Properties |
|---|---|---|---|---|---|---|
| IV-34 | Cl | Cl | H | H | -CH₂-CH(CH₃)-phenyl | |
| IV-35 | Cl | Cl | H | H | -CH=CH-phenyl | |
| IV-36 | Cl | Cl | H | H | -C(CH₃)=CH-phenyl | |
| IV-37 | Cl | Cl | H | H | 1-naphthyl | |
| IV-38 | Cl | Cl | H | H | 2-naphthyl | |
| IV-39 | Cl | Cl | H | H | 1-methyl-2-methoxy-naphthyl | |
| IV-40 | Cl | Cl | H | H | phenyl | mp 119–120° C. |
| IV-41 | Cl | Cl | C₂H₅ | H | phenyl | mp 143–146° C. |
| IV-42 | Cl | Cl | H | H | 4-methylphenyl | |
| IV-43 | Cl | Cl | H | H | 2-(trifluoromethyl)phenyl | |
| IV-44 | Cl | Cl | H | H | 2-fluorophenyl | |

TABLE 2-continued
(IV)
| Compound No. | X | Y | R¹ | R² | R³ | | Physical Properties |
|---|---|---|---|---|---|---|---|
| IV-45 | Cl | Cl | H | H | 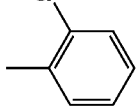 | | |
| IV-46 | Cl | Cl | H | H | 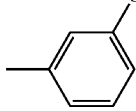 | | $n^D_{20}$ 1.6068 |
| IV-47 | Cl | Cl | H | H |  | | |
| IV-48 | Cl | Cl | H | H | 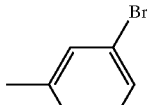 | | |
| IV-49 | Cl | Cl | H | H |  | | |
| IV-50 | Cl | Cl | H | H |  | | |
| IV-51 | Cl | Cl | H | H |  | | |
| IV-52 | Cl | Cl | H | H | 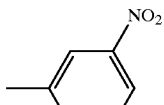 | | mp 137–138° C. |
| IV-53 | Cl | Cl | H | H | 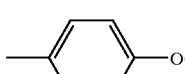 | | |
| IV-54 | Cl | Cl | H | H | 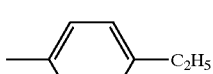 | | |
| IV-55 | Cl | Cl | H | H |  | | |

TABLE 2-continued (IV) Structure: isothiazole with X, Y substituents, C(=O)-N(R¹)-C(R²)(R³)(CN)

| Compound No. | X | Y | R¹ | R² | R³ | Physical Properties |
|---|---|---|---|---|---|---|
| IV-56 | Cl | Cl | H | H | 4-(iso-C₃H₇)-C₆H₄- | |
| IV-57 | Cl | Cl | H | H | 4-(tert-C₄H₉)-C₆H₄- | |
| IV-58 | Cl | Cl | H | H | 4-N(CH₃)₂-C₆H₄- | |
| IV-59 | Cl | Cl | H | H | 4-biphenylyl | |
| IV-60 | Cl | Cl | H | H | 3-(phenoxy)-C₆H₄- | |
| IV-61 | Cl | Cl | H | H | 4-(benzyloxy)-C₆H₄- | |
| IV-62 | Cl | Cl | H | H | 2-F-4-CF₃-C₆H₃- | |
| IV-63 | Cl | Cl | H | H | 2,4-F₂-C₆H₃- | |
| IV-64 | Cl | Cl | H | H | 2,3-Cl₂-C₆H₃- | |
| IV-65 | Cl | Cl | H | H | 2,4-Cl₂-C₆H₃- | |

TABLE 2-continued (IV)

[Structure: 3-X, 4-Y substituted isothiazole-5-carboxamide with N-R¹ and C(R²)(R³)(CN) group]

| Compound No. | X | Y | R¹ | R² | R³ | Physical Properties |
|---|---|---|---|---|---|---|
| IV-66 | Cl | Cl | H | H | 2,3-dichlorophenyl | |
| IV-67 | Cl | Cl | H | H | 3,4-dichlorophenyl | |
| IV-68 | Cl | Cl | H | H | 2-chloro-6-fluorophenyl (3-chloro-2-fluorophenyl) | |
| IV-69 | Cl | Cl | H | H | 2,4-dimethoxyphenyl | |
| IV-70 | Cl | Cl | H | H | 2,5-dimethoxyphenyl | |
| IV-71 | Cl | Cl | H | H | 3,5-dimethoxyphenyl | |
| IV-72 | Cl | Cl | H | H | 3,4-methylenedioxyphenyl | |
| IV-73 | Cl | Cl | H | H | 4-chloro-3-nitrophenyl | |

TABLE 2-continued (IV)

| Compound No. | X | Y | R¹ | R² | R³ | Physical Properties |
|---|---|---|---|---|---|---|
| IV-74 | Cl | Cl | H | H | 2,4-dinitrophenyl | |
| IV-75 | Cl | Cl | H | H | 2,4-dimethylphenyl | |
| IV-76 | Cl | Cl | H | H | 3,4,5-trimethoxyphenyl | |
| IV-77 | Cl | Cl | H | H | 2-bromo-4,5-dimethoxyphenyl | |
| IV-78 | Cl | Cl | H | H | 4,5-dimethyl-2-nitrophenyl | |
| IV-79 | Cl | Cl | H | H | 6-methyl-5-nitro-1,3-benzodioxol-yl | |
| IV-80 | Cl | Cl | H | H | 2,3,5-trichlorophenyl | |

TABLE 2-continued (IV)

Structure: Isothiazole ring with X at 3-position, Y at 4-position, and C(=O)-N(R¹)-C(R²)(R³)(CN) at 5-position.

| Compound No. | X | Y | R¹ | R² | R³ | Physical Properties |
|---|---|---|---|---|---|---|
| IV-81 | Cl | Cl | H | | cyclopentyl, H | |
| IV-82 | Cl | Cl | H | | cyclohexyl, H | |
| IV-83 | Cl | Cl | H | | 4,4-dimethylcyclohexyl, H | |
| IV-84 | Cl | Cl | H | | 1-methylpiperidin-4-yl | |
| IV-85 | Cl | Cl | H | H | 1-methylpyrrol-2-yl | |
| IV-86 | Cl | Cl | H | H | furan-2-yl | |
| IV-87 | Cl | Cl | H | H | furan-3-yl | |
| IV-88 | Cl | Cl | H | H | furan-3-yl | |
| IV-89 | Cl | Cl | H | H | 5-nitrofuran-2-yl | |
| IV-90 | Cl | Cl | H | H | 5-methylfuran-2-yl | |
| IV-91 | Cl | Cl | H | H | 5-bromofuran-2-yl | |
| IV-92 | Cl | Cl | H | H | thiophen-2-yl | |

TABLE 2-continued
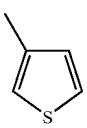
(IV)
| Compound No. | X | Y | R¹ | R² | R³ | Physical Properties |
|---|---|---|---|---|---|---|
| IV-93 | Cl | Cl | H | H | 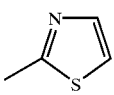 | |
| IV-94 | Cl | Cl | H | H | 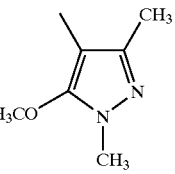 | |
| IV-95 | Cl | Cl | H | H | 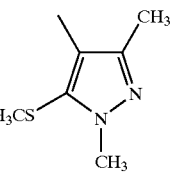 | |
| IV-96 | Cl | Cl | H | H | 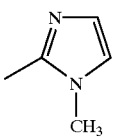 | |
| IV-97 | Cl | Cl | H | H | 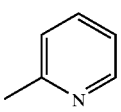 | |
| IV-98 | Cl | Cl | H | H | 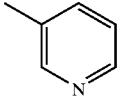 | |
| IV-99 | Cl | Cl | H | H | 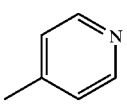 | |
| IV-100 | Cl | Cl | H | H | 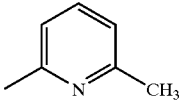 | |
| IV-101 | Cl | Cl | H | H | 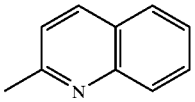 | |
| IV-102 | Cl | Cl | H | H |  | |

TABLE 2-continued (IV)

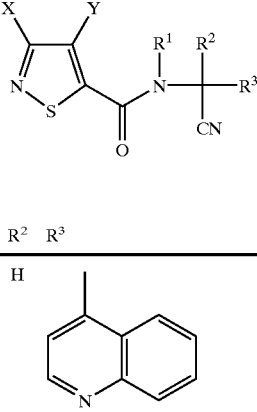

| Compound No. | X | Y | $R^1$ | $R^2$ | $R^3$ | Physical Properties |
|---|---|---|---|---|---|---|
| IV-103 | Cl | Cl | H | H | 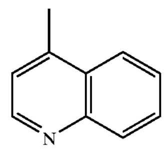  | |

BIOLOGICAL TEST EXAMPLES
Test Example A
Test of foliar spray effect against Pyricularia oryzae
Preparation of Formulations of the Compounds Tested

Active compound: 30–40 parts by weight

Carrier: mixture of diatomaceous earth and kaolin (1:5), 55–65 parts by weight

Emulsifier: polyoxyethylene alkyl phenyl ether, 5 parts by weight

The above-mentioned amounts of active compound, carrier and emulsifier are crushed and mixed to make a wettable powder. A portion of the wettable powder comprising the prescribed amount of active compound is diluted with water and used for testing.

Testing Procedure

Seedlings of paddy rice (cultivar:Kusabue) were cultured in plastic pots each having a diameter of 6 cm. The previously prepared solution of the prescribed concentration of active compound was sprayed over the seedlings in the 1.5–2 leaf stage, at a rate of 25 ml per 3 pots 5 days after the application, a suspension of spores of artificially cultured *Pyricularia oryzae* was spray-inoculated once on the seedlings, and the seedlings were maintained at 25° C. and 100% relative humidity for infection, 7 days after the inoculation, the contraction rate per pot was classified and evaluated according to the following standard and the control value (%) was calculated. Phytotoxicity was tested at the same time. This test is an average of the results of 1 section 3 pots. The evaluation of the contraction rate and the calculation method of the control value are identical in each of the Test Examples 1–3.

| Contraction rate | Percentage of lesion area in (%) |
|---|---|
| 0 | 0 |
| 0.5 | less than 2 |
| 1 | 2-less than 5 |
| 2 | 5-less than 10 |
| 3 | 10-less than 20 |
| 4 | 20-less than 40 |
| 5 | more than 40 |

$$\text{Control value (\%)} = \left(1 - \frac{\text{Contraction rate of treated section}}{\text{Contraction rate of untreated section}}\right) \times 100$$

Test Results

Compounds No. 1, 3, 4, 5, 7, 8, 10, 13, 16, 17, 20, 30, 32, 33, 34, 35, 38, 39, 55 64, 111 and 122 showed control values of more than 80% at an active compound concentration of 500 ppm. No phytotoxicity was observed.

Test Example B

Test of water surface application effect against Pyricularia oryzae:

Testing Procedure

Seedlings of paddy rice (cultivar: Kusabue) in the 1.5 leaf stage were transplanted into irrigated plastic pots (30 $cm^2$), one seedling per pot. 7 days after the transplanting (when the seedlings were in 3–4 leaf stage), the solution of the prescribed concentration of the active compound, which had been prepared in the manner similar to that of Test Example A, was dropped to the water surface with a pipette at a rate of 5 ml per pot. 7 days after the chemical treatment, a suspension of spores of artificially cultured *Pryricularia*

*oryzae* (C race) was spray-inoculated once on the seedlings, and the seedlings were maintained in the inoculation box at 25° C. and 100% relative humidity for 12 hours for infection. Thereafter, the seedlings were transferred to the greenhouse for management. 7 days after the inoculation, the contraction rate per pot was evaluated and further the control value (%) was calculated. Phytotoxicity was tested at the same time.

Test Results

Compounds No. 1, 2, 3, 4, 5, 6, 7, 8, 10, 13, 14, 16, 21, 30, 32, 33, 34, 35, 38, 39, 55, 64 and 111 showed control values of more than 80% at an active compound concentration of 8 kg/ha.

Test Example C

Spraying test against Phytophthora infestans.

Testing Procedure

About 1 seed of tomato (cultivar: Regina) was sown in each plastic pot of a diameter of 7 cm, and raised in a greenhouse at 15–25° C. The solution obtained by diluting the prepared formulation of the test compound to the prescribed concentration as mentioned above, was sprayed at a rate of 25 ml per 3 pots over small seedlings reaching the 4 leaf stage. Zoosporangia formed on the lesion of previously infected phytophthora infestans was washed down with a brush into distilled water to make a suspension. 5 days after the spraying, the suspension was inoculated by spraying to the plants to be treated and kept in a greenhouse of 15–20° C. 4 days after the inoculation, the contraction rate per pot was classified and the control value was calculated. The result is an average of 3 pots. Phytotoxicity was tested at the same time.

Test Results

Compounds No. 1, 3, 4, 5, 6, 7, 8, 10, 13, 16, 20, 30, 32, 33, 38, 40, 55, 64, 111 and 122 showed control values of more than 80% at an active compound concentration of 500 ppm. No phytotoxicity was observed.

FORMULATION EXAMPLES

Formnulation Example I (Granules)

25 parts by weight of water were added to a mixture of 10 parts by weight of Compound No. 8 according to the invention, 30 parts by weight of bentonite (montmorillonite), 58 parts by weight of talc and 2 parts by weight of lignin sulphonic acid salt, and the mixture was kneaded thoroughly. The resulting product was granulated by means of an extrusion granulator to form granules having a size of from 10 to 40 meshes. The granules were dried at a temperature between 40 and 50° C.

Formulation Example II (Granules)

95 parts by weight of a clay mineral having a particle size distribution within a range of from 0.2 to 2 mm were introduced into a rotary mixer. This product was uniformly wetted by spraying thereto under rotation a mixture of 5 parts by weight of Compound No. 14 according to the invention and a liquid diluent. The granules obtained in this manner were dried at a temperature between 40 and 50° C.

Formulation Example III (Emulsifiable Concentrate)

An emulsifiable concentrate was prepared by mixing 30 parts by weight of Compound No. 17 according to the invention, 55 parts by weight of xylene, 8 parts by weight of polyoxyethylene alkyl phenyl ether and 7 parts by weight of calcium alkylbenzene sulphonate with stirring.

Formulation Example IV (Wettable Powder)

A wettable powder was prepared by thoroughly mixing 15 parts by weight of Compound No. 35 according to the invention, 80 parts by weight of a mixture (1:5) of White Carbon (fine powder of hydrated non-crystalline silicon oxide) and powdery clay, 2 parts by weight of sodium alkylbenzene sulphonate and 3 parts by weight of a condensate of sodium alkylnaphthalene sulphonate and formaldehyde in powdery state.

Formulation Example V (Wettable Granules)

20 parts by weight of Compound No. 40 according to the invention, 30 parts by weight of sodium lignin sulphonate, 15 parts by weight of bentonite and 35 parts by weight of calcined diatomaceous earth powder were thoroughly mixed with water. The resulting product was granulated by means of extrusion through a 0.3 mm screen. After drying the product, wettable granules were obtained.

What is claimed is:

1. An isothiazolecarboxamide of the formula

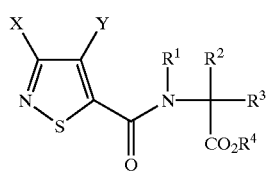

(I)

wherein

X represents fluoro, chloro, bromo, methyl, ethyl or trifluoromethyl,

Y represents a hydrogen atom, fluoro, chloro, bromo, cyano, methoxycarbonyl or ethoxycarbonyl, $R^1$ represents a hydrogen atom, $R^2$ represents a hydrogen atom or methyl, $R^4$ represents methyl or ethyl, $R^3$ represents a hydrogen atom, $C_{1-12}$ alkyl, $C_{3-6}$ cycloalkyl, $C_{2-6}$ alkenyl which may be substituted with phenyl, or $R^3$ represents $C_{5-6}$ cycloalkenyl, $C_7$ bicycloalkenyl, C1-2 haloalkyl, or $R^3$ represents $C_{1-4}$ alkyl, which is substituted with 1 or 2 substituents selected from the group consisting of hydroxy, $C_{1-4}$ alkoxy, mercapto, $C_{1-4}$ alkylthio, $C_{1-4}$ alkylsulfinyl, $C_{1-4}$ alkylsulfonyl, phenyl and a 5-membered heterocyclic ring having 1–3 nitrogen atoms which may be benzo-condensed, or $R^3$ represents phenyl, which may be substituted with 1 to 4 groups selected from the group consisting of $C_{1-4}$ alkyl, halogen, $C_{1-4}$ haloalkyl, $C_{1-4}$ haloalkoxy, nitro, cyano, $C_{1-4}$ alkoxy, benzyloxy, phenoxy, $C_{1-4}$ alkylenedioxy, $C_{1-4}$ alkylthio, di-$C_{1-4}$ alkyl-amino and phenyl, or $R^3$ represents naphtyl, which may be substituted with methoxy, or $R^3$ represents a 5- or 6-membered heterocyclic group, which has 1 to 3 heteroatoms selected from the group consisting of nitrogen, oxygen and sulfur, which heterocyclic groups may be benzo-condensed and may be substituted with 1 to 3 substituents selected from the group consisting of $C_{1-4}$ alkyl, halogen $C_{1-4}$ alkoxy, $C_{1-4}$ alkylthio and nitro,
or
$R^2$ and $R^3$, together with the carbon atom to which they are bonded, form a $C_{5-6}$ cycloalkyl, which may be substituted with 1 or 2 methyl groups, or $R^2$ and $R^3$, together with the carbon atom to which they are bonded, form a 5- or 6-membered heterocyclic ring, which comprises one nitrogen atom and which may be substituted with 1 or 2 methyl groups, or $R^2$ and $R^3$, together with the carbon atom to which they are bonded, form a group of the formula C=CH—$R^5$, in which $R^5$ represents a hydrogen atom, methyl or ethyl,
or
$R^3$ and $R^4$, together with the carbon atom and the carboxyl group to which they are bonded, form a 5- or 6-membered heterocyclic ring having one ring-constituting oxygen atom and being substituted with one oxo group, with the proviso, however, that
$R^3$ does not represent isopropyl,
if
X and Y represent chloro, and
$R^2$ represents a hydrogen atom.

2. An isothiazolecarboxamide of the formula (I) according to claim 1, wherein

X represents chloro or methyl,
Y represents a hydrogen atom, chloro or cyano,
$R^1$ represents a hydrogen atom
$R^2$ represents a hydrogen atom or methyl,
$R^4$ represents methyl or ethyl,
$R^3$ represents a hydrogen atom, $C_{1-12}$ alkyl, cyclopropyl, cyclohexyl, vinyl, allyl, 1-propenyl, 1-methylvinyl, 2-methyl-1-propenyl, 1-pentenyl, 1-methyl-1-pentenyl, 1-n-butyl-vinyl, 2-phenyl-vinyl, 1-methyl-2-phenyl-vinyl, 3-cyclohexenyl, 5-norbornen-2-yl, chloromethyl, trifluoromethyl, hydroxymethyl, 1-hydroxyethyl, methoxymethyl, mecaptomethyl, methylthiomethyl, methylthioethyl, methylsulfinylethyl, methylsulfonylmethyl, benzyl, α-methylbenzyl, phenethyl, 2-methylphenethyl, 4-imidazolylmethyl, 3-indolylmethyl, or
$R^3$ represents phenyl, which may be substituted with 1 to 3 groups selected from the group consisting of methyl, ethyl, n-propyl, isopropyl, tert-butyl, fluoro, chloro, bromo, trifluoromethyl, trifluoromethoxy, cyano, methoxy, benzyloxy, phenoxy, methylenedioxy, methylthio, nitro, dimethylamino and phenyl, or
$R^3$ represents 1-naphtyl, 2-naphthyl, 2-methoxy-1-naphthyl, or
$R^3$ represents a 5- or 6 membered heterocyclic group with 1 or 2 heteroatoms selected from nitrogen, oxygen and sulfur, which heterocyclic groups may be benzo-condensed and may be substituted with 1 to 3 substituents selected from methyl, chloro, bromo, methoxy, methylthio and nitro, or
$R^2$ and $R^3$, together with the carbon atom to which they are bonded, form a group selected from cyclopentyl, cyclohexyl, 4,4-dimethyl-cyclohexyl, N-methyl-piperidin-4-yl and vinylidene, or $R^3$ and $R^4$, together with the carbon atom and the carboxyl group to which they are bonded, form a 1-oxo-2-tetrahydrofuryl group, with the proviso, however, that
$R^3$ does not represent isopropyl,
if
X and Y represent chloro, and
$R^2$ represents a hydrogen atom.

3. A process for the preparation of an isothiazolecarboxamide of the formula (I) according to claim 1, comprising reacting
a) an isothiazolecarboxylic acid chloride of the formula

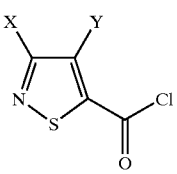

(II)

wherein
X and Y are as defined in claim 1,
with an amine of the formula

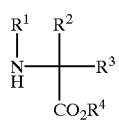

(III)

wherein
$R^1$, $R^2$, $R^3$ and $R^4$ are as defined in claim 1,
in the presence of an inert diluent, or
b) an isothiazolecarboxylic acid derivative of the formula

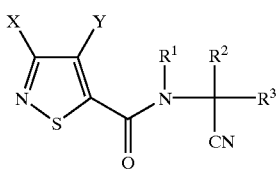

(IV)

wherein
X, Y, $R^1$, $R^2$, and $R^3$ are as defined in claim 1,
with a compound of the formula

HO—$R^4$ (V)

wherein
$R^4$ is as defined in claim 1,
in the presence of an inert diluent.

4. A microbicidal composition comprising an isothiazolecarboxamide of the formula (I) according to claim 1 plus extenders and/or surface active agents.

5. A process for combating undesired microorganisms, comprising applying an isothiazolecarboxamide of the formula (I) according to claim 1 to the microorganisms and/or to their habitat.

6. A process for the preparation of microbicidal compositions, comprising mixing an isothiazolecarboxamide of the formula (I) according to claim 1 with extenders and/or surface-active agents.

7. An isothiazolecarboxamide according to claim 1, wherein

R³ represents a hydrogen atom, unsubstituted $C_{1-12}$ alkyl, unsubstituted $C_{3-6}$ cycloalkyl, unsubstituted or phenyl-substituted $C_{2-6}$ alkenyl.

8. An isothiazolecarboxamide according to claim 1, wherein

R³ represents $C_{5-6}$ cycloalkenyl, $C_7$ bicycloalkenyl, $C_{1-2}$ haloalkyl.

9. An isothiazolecarboxamide according to claim 1, wherein

R³ represents a mono- or di-substituted $C_{1-4}$ alkyl, wherein the substituents are selected from the group consisting of hydroxy, $C_{1-4}$ alkoxy, mercapto, $C_{1-4}$ alkylthio, $C_{1-4}$ alkylsulfinyl, $C_{1-4}$ alkylsulfonyl, and phenyl.

10. An isothiazolecarboxamide according to claim 1, wherein

R³ represents unsubstituted or mono-, di- tri- or tetra-substituted phenyl, wherein the substitutents are selected from the group consisting of $C_{1-4}$ alkyl, halogen, $C_{1-4}$ haloalkyl, $C_{1-4}$ haloalkoxy, nitro, cyano, $C_{1-4}$ alkoxy, benzyloxy, phenoxy, $C_{1-4}$ alkylenedioxy, $C_{1-4}$ alkylthio, di-$C_{1-4}$ alkyl-amino and phenyl.

11. An isothiazolecarboxamide according to claim 2, wherein

R³ represents a hydrogen atom, $C_{1-12}$ alkyl, cyclopropyl, cyclohexyl, vinyl, allyl, 1-propenyl, 1-methylvinyl, 2-methyl-1-propenyl, 1-pentenyl, 1-methyl-1-pentenyl, 1-n-butyl-vinyl, 2-phenyl-vinyl, 1-methyl-2-phenyl-vinyl, 3-cyclohexenyl, 5-norbornen-2-yl, chloromethyl, trifluoromethyl, hydroxymethyl, 1-hydroxyethyl, methoxymethyl, mecaptomethyl, methylthiomethyl, methylthioethyl, methylsulfinylethyl, methylsulfonylmethyl, benzyl, α-methylbenzyl, phenethyl, 2-methylphenethyl, 4-imidazolylmethyl, or 3-indolylmethyl.

12. An isothiazolecarboxamide according to claim 2, wherein

R³ represents unsubstituted or mono- di- or tri-substituted phenyl, wherein the substituents are selected from the group consisting of methyl, ethyl, n-propyl, isopropyl, tert-butyl, fluoro, chloro, bromo, trifluoromethyl, trifluoromethoxy, cyano, methoxy, benzyloxy, phenoxy, methylene-dioxy, methylthio, nitro, dimethylamino and phenyl.

13. An isothiazolecarboxamide according to claim 2, wherein

R³ represents 1-naphtyl, 2-naphthyl, 2-methoxy-1-naphthyl.

* * * * *